United States Patent

Aumueller et al.

Patent Number: 5,248,778
Date of Patent: Sep. 28, 1993

[54] POLYALKYLPIPERIDINE COMPOUNDS

[75] Inventors: Alexander Aumueller, Deidesheim, Fed. Rep. of Germany; Hubert Trauth, Dudenhofen, both of Fed. Rep. of Germany

[73] Assignee: BASF Aktiengesellschaft, Ludwigshafen, Fed. Rep. of Germany

[21] Appl. No.: 775,756

[22] Filed: Oct. 15, 1991

[30] Foreign Application Priority Data

Oct. 16, 1990 [DE] Fed. Rep. of Germany ....... 4032744

[51] Int. Cl.$^5$ .......................................... C07D 401/12
[52] U.S. Cl. .................... 546/186; 546/244; 546/209; 546/210; 546/193; 544/129; 544/364
[58] Field of Search ............... 546/244, 186, 209, 210, 546/193; 544/129, 364

[56] References Cited

U.S. PATENT DOCUMENTS

| | | | |
|---|---|---|---|
| 4,530,950 | 7/1985 | Raspanti et al. | 524/100 |
| 4,604,393 | 8/1986 | Cornu et al. | 514/235.5 |
| 4,976,889 | 12/1990 | Aumueller et al. | 252/403 |

OTHER PUBLICATIONS

J. Chem. Soc. 1948, F. H. S. Curd et al., pp. 1630–1636, "Synthetic Antimalarials".
Fortschr. Chem. Forsch, Bd. Oct. 3, (1968), The Chemistry of Biguanides, Dr. F. Kurzer et al., pp. 375–473.

*Primary Examiner*—C. Warren Ivy
*Assistant Examiner*—Zinna N. Davis
*Attorney, Agent, or Firm*—Oblon, Spivak, McClelland, Maier & Neustadt

[57] ABSTRACT

A polyalkylpiperidine derivative of formula I

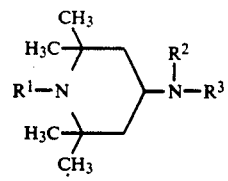

where
$R^1$ is hydrogen, $C_1$–$C_8$-alkyl, phenyl- or tolylalkyl with 1 to 4 carbon atoms in the alkyl, $C_1$–$C_6$-acyl, benzoyl, allyl, cyanomethyl, hydroxyethyl, aminoethyl, hydroxyl or oxyl free radical,
$R^2$ is a radical of the formula:

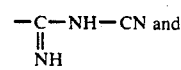

$R_3$ is hydrogen, $C_1$–$C_{22}$-alkyl, $C_3$–$C_{22}$-alkenyl, $C_7$–$C_{22}$-phenyl- and diphenylalkyl, where the phenyl can be unsubstituted or substituted one to three times by $C_1$–$C_{12}$-alkyl, $C_1$–$C_{12}$-alkoxy, fluorine, chlorine, bromine, $C_3$–$C_{12}$-alkylamino or $C_1$–$C_{12}$-dialkylamino, or is $C_3$–$C_{12}$-cycloalkyl or bicycloalkyl, $C_4$–$C_{22}$-alkyl which is interrupted by oxygen or nitrogen atoms and which can additionally carry hydroxyl groups, phenyl which can be substituted by one to three methyl or carbo-$C_1$–$C_{12}$-alkoxy groups, or is $C_1$–$C_{22}$-alkyl containing heterocyclic radicals, or is a radical of the formula:

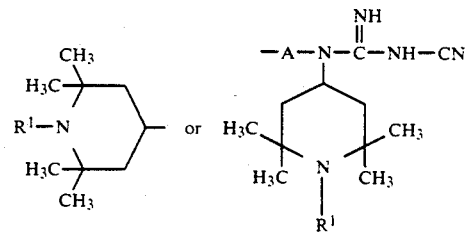

The polyalkylpiperidine compound is useful as a UV stabilizer and as a stabilizer for organic material.

6 Claims, No Drawings

POLYALKYLPIPERIDINE COMPOUNDS

The present invention relates to novel polyalkylpiperidine derivatives of the formula 1

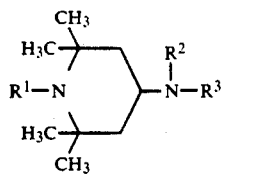

where
$R^1$ is hydrogen, $C_1$-$C_8$-alkyl, $C_1$ phenyl- or tolylalkyl with 1 to 4 carbon atoms in the alkyl, $C_1$-$C_6$-acyl, benzoyl, allyl, cyanomethyl, hydroxyethyl, aminoethyl, hydroxyl or oxyl free radical,
$R^2$ is a radical of the formula (a)

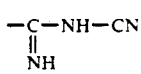

a radical of the formula (b)

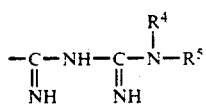

or a radical of the formula (ca)

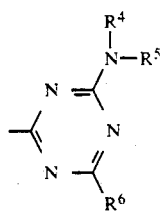

where
$R^4$ and $R^5$ are each hydrogen, $C_1$-$C_{22}$-alkyl, $C_3$-$C_{22}$-alkenyl, $C_7$-$C_{22}$-phenyl- and diphenylalkyl, where the phenyl can be unsubstituted or substituted one to three times by $C_1$-$C_{12}$-alkyl, $C_1$-$C_{12}$-alkoxy, fluorine, chlorine, bromine, $C_1$-$C_{12}$-alkylamino or $C_1$-$C_{12}$-dialkylamino, or are $_3$-$C_{12}$-cycloalkyl, $C_3$-$C_{22}$-alkyl which is interrupted in the chain by oxygen or nitrogen atoms and which can additionally carry hydroxyl groups, or are phenyl which is unsubstituted or substituted one to four times by $C_1$-$C_{12}$-alkyl, $C_3$-$C_{12}$-cycloalkyl, $C_1$-$C_{12}$-alkoxy, chlorine, bromine, $C_1$-$C_{12}$-alkylamino, $C_1$-$C_{12}$-dialkylamino, phenyl, benzyl, hydroxyl or cyano, or are a 5- or 6-membered aromatic heterocycle, with the proviso that at least one of $R^4$ or $R^5$ is aromatic, and
$R^6$ is hydrogen, $C_1$-$C_{22}$-alkyl, $C_2$$C_{22}$-alkenyl, $C_7$-$C_{22}$-phenyl- and diphenylalkyl, where the phenyl can be unsubstituted or substituted one to three times by $C_1$-$C_{12}$-alkyl, $C_1$-$C_{12}$-alkoxy, chlorine, bromine, $C_1$-$C_{12}$-alkylamino, $C_1$-$C_{12}$-dialkylamino, hydroxyl, cyano or $C_1$-$C_{12}$-carboalkoxy, or is phenyl which can be unsubstituted or substituted one to three times by $C_1$-$C_{12}$-alkyl, $C_1$-$C_{12}$-alkoxy, chlorine, bromine, phenyl, $C_1$-$C_{12}$-alkylamino, $C_1$-$C_{12}$-dialkylamino, hydroxyl, cyano, $C_1$-$C_{12}$-carbonyloxy or $C_1$-$C_{12}$-carboalkoxy, or is $C_3$-$C_{12}$-cycloalkyl, pyridyl, or $C_2$-$C_{22}$-alkyl which is interrupted by carbonyloxy, or a radical of the formula

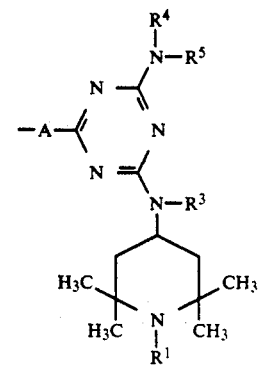

where A is $C_2$-$C_{22}$-alkylene, $C_8$-$C_{22}$-cycloalkylene, $C_8$-$C_{16}$-phenylalkylene, phenylene or $C_4$-$C_{30}$-alkylene which is interrupted in the chain by oxygen or nitrogen atoms or 5- or 6-membered heterocycles, and
$R^3$ is hydrogen, $C_1$-$C_{22}$-alkyl, $C_3$-$C_{22}$-alkenyl, $C_7$-$C_{22}$-phenyl- and diphenylalkyl, where the phenyl can be unsubstituted or substituted one to three times by $C_1$-$C_{12}$-alkyl, $C_1$-$C_{12}$-alkoxy, fluorine, chlorine, bromine, $C_1$-$C_{12}$-alkylamino or $C_1$-$C_{12}$-dialkylamino, or is $C_3$-$C_{12}$-cycloalkyl or bicycloalkyl, $C_4$-$C_{22}$-alkyl which is interrupted by oxygen or nitrogen atoms and which can additionally carry hydroxyl groups, phenyl which can be substituted by one to three methyl or carbo-$C_1$-$C_{12}$-alkoxy groups, or is $C_1$-$C_{22}$-alkyl containing heterocyclic radicals, or is a radical of the formula

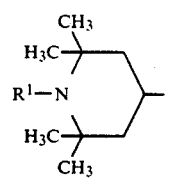

or, when $R^2$ is the radical (a), a radical of the formula

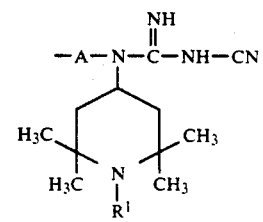

or, when $R^2$ is the radical (b), a radical of the formula

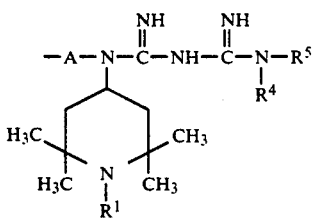

or, when $R^2$ is the radical (c), a radical of the formula

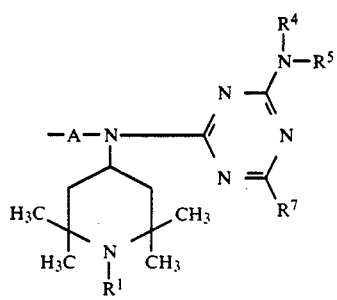

where $R^7$ is hydrogen, $C_1$–$C_{22}$-alkyl, $C_2$–$C_{22}$-alkenyl, $C_7$–$C_{22}$-phenyl- and diphenylalkyl, where the phenyl can be unsubstituted or substituted one to three times by $C_1$–$C_{12}$-alkyl, $C_1$–$C_{12}$-alkoxy, chlorine, bromine, $C_1$–$C_{12}$-alkylamino, $C_1$–$C_{12}$-dialkylamino, hydroxyl, cyano or $C_1$–$C_{12}$-carboalkoxy, or is phenyl which can be unsubstituted or substituted one to three times by $C_1$–$C_{12}$-alkyl, $C_1$–$C_{12}$-alkoxy, chlorine, bromine, phenyl, $C_1$–$C_{12}$-alkylamino, $C_1$–$C_{12}$-dialkylamino, hydroxyl, cyano, $C_1$–$C_{12}$-carbonyloxy or $C_1$–$C_{12}$-carboalkoxy, or is $C_3$–$C_{12}$-cycloalkyl, pyridyl, or $C_2$–$C_{22}$-alkyl interrupted by carbonyloxy,
and tautomers and acid addition salts of the compound I.

DE-A 33 04 266 (1) relates to piperidine derivatives of the formula II

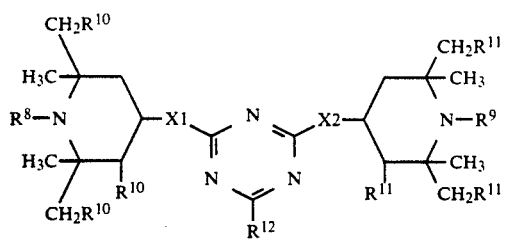

where $R^8$ to $R^{12}$ are each hydrogen or hydrocarbon radicals, and $X^1$ and $X^2$ are each oxygen- or nitrogen-containing bridges. The compounds II are recommended as stabilizers for polymers.

Organic material, especially plastics and coating compositions, are, as is known, very rapidly damaged especially by the action of light. This damage is normally evident from the material becoming discolored, fissured or brittle. The UV absorbers and stabilizers used to date have not provided satisfactory protection against damage to organic materials by light, oxygen and heat.

It is an object of the present invention to prepare UV absorbers and stabilizers which provide effective protection for organic material.

We have found that this object is achieved by the polyalkylpiperidine derivatives I defined above.

Besides hydrogen, suitable for $R^1$ are, in particular, methyl, ethyl, propyl, butyl, pentyl, hexyl, benzyl, $\beta$-phenylethyl, $\gamma$-phenylpropyl, o-, m- or p-methylbenzyl, allyl, acetyl, propionyl, butanoyl, pentanoyl, benzoyl, cyanomethyl, $\beta$-hydroxyethyl, $\beta$-aminoethyl and hydroxyl, and nitrosyl. Of these, methyl, acetyl, cyanomethyl, $\beta$-aminoethyl and, in particular, hydrogen are particularly preferred.

The compounds I where $R^2$ is a radical of the formula (a) are cyanoguanidine derivatives, those where $R^2$ is a radical of the formula (b) are biguanide derivatives and those where $R^2$ is a radical of the formula (c) are triazine derivatives.

Examples of meanings of $R^3$ are, besides hydrogen, the following:

straight-chain and branched $C_1$–$C_{22}$-alkyl such as methyl, ethyl, n- and i-propyl, n- and i-butyl, n- and i-pentyl, hexyl, octyl, decyl, dodecyl, tetradecyl, hexadecyl, octadecyl, pivalyl, 3,3-dimethyl-2-butyl, neopentyl, 4-methyl-2-pentyl and 2-ethylhexyl;

$C_3$–$C_{22}$-alkenyl such as allyl, butenyl, pentenyl and oleyl;

$C_3$–$C_{12}$-cycloalkyl such as cyclopropyl, cyclobutyl, cyclopentyl, cyclohexyl, methylcyclohexyl, cycloheptyl, cyclooctyl, cyclododecyl and bicycloheptyl, of these cyclopentyl and, especially, cyclohexyl are preferred;

$C_4$–$C_{22}$-alkyl which is interrupted in the chain by oxygen or nitrogen atoms and which can additionally carry hydroxyl groups, such as —$(CH_2)_3N(CH_3)_2$, —$(CH_2)_3N(C_2H_5)_2$, —$(CH_2)_3$—$OCH_3$, —$(CH_2)_3$—$O$—$CH(CH_3)_2$, —$(CH_2)_2$—$O$—$(CH_2)_2$—$OH$, —$CH_2$—$(CH_2)_2$—$CH_2$—$N(CH_3)_2$, —$(CH_2)_2$—$N[CH(CH_3)_2]_2$, —$(CH_2)_2$—$N(C_2H_5)_2$, —$(CH_2)_2$—$N(CH_3)_2$, —$(CH_2)_2$—$OCH_3$ and —$(CH_2)_2OCH_2CH_3$;

substituted or unsubstituted $C_7$–$C_{22}$-phenyl- and diphenylalkyl such as benzyl, methoxybenzyl, methylbenzyl, ethylbenzyl, isopropylbenzyl, trimethylbenzyl, fluorobenzyl, chlorobenzyl, methylenedioxybenzyl, $\beta$-phenylethyl, $\gamma$-phenylpropyl and $\delta$-phenylbutyl, dimethylaminobenzyl, diphenylmethyl and 1,3-diphenyl-2-propyl, where the substitution pattern on the phenyl can be o, m or p in each case;

substituted or unsubstituted phenyl such as phenyl, o-, m- or p-tolyl or phenyl substituted by carbo—$C_1$–$C_{12}$-alkoxy, such as o-, m- or p-carbomethoxyphenyl;

a radical of the formula

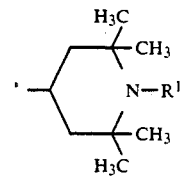

heterocyclo-containing $C_1$–$C_{22}$-alkyl such as

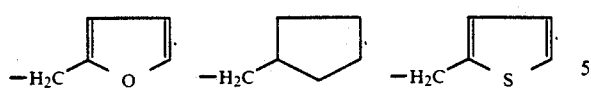

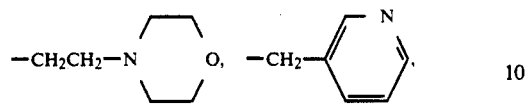

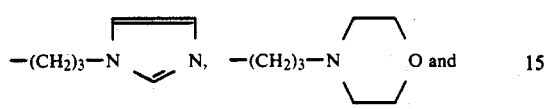

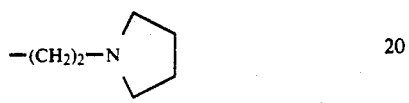

When $R^2$ is (a), $R^3$ can also be a radical of the formula

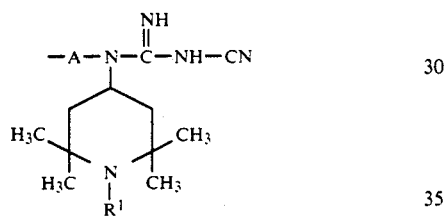

when $R^2$ is (b), $R^3$ can also be a radical of the formula

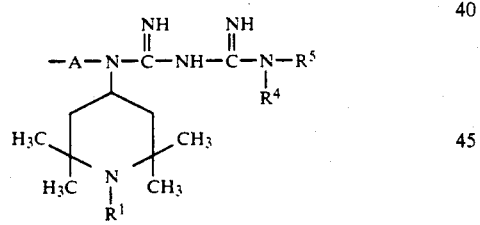

and when $R^2$ is (c), $R^3$ can also be a radical of the formula

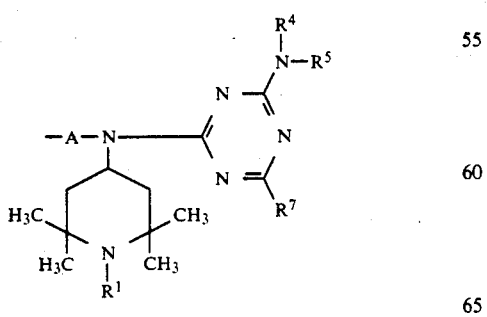

where $R^7$ in the last formula has the same meaning as $R^6$ with the exception of the radical of the formula

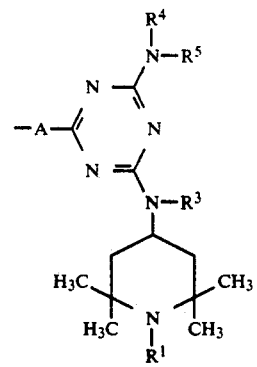

Suitable meanings for the bridge A are the following:

—$C_2$—$C_{22}$-alkylene and $C_5$—$C_{22}$-cycloalkylene such as
—$(CH_2)_p$—$CH_2$— (with p = 1 to 21),

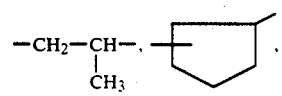

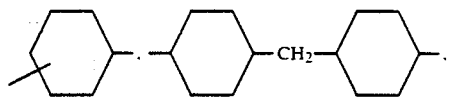

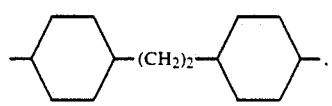

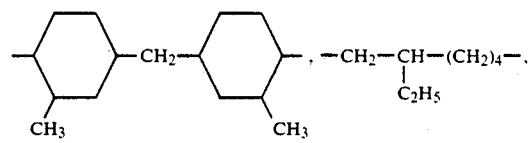

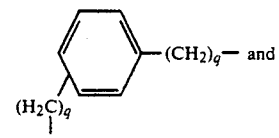

—$C_8$—$C_{16}$-phenylalkylene and phenylene such as

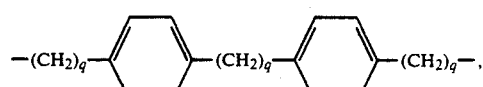

with q =0-4

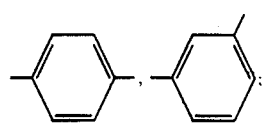

-continued

—C$_4$—C$_{30}$-alkylene which is interrupted in the chain by oxygen or nitrogen atoms or heterocycles, such as
—(CH$_2$)$_3$O(CH$_2$)$_4$O(CH$_2$)$_3$—,
—(CH$_2$)$_3$O(CH$_2$)$_2$O(CH$_2$)$_2$O(CH$_2$)$_3$—,

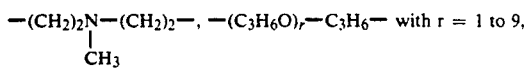

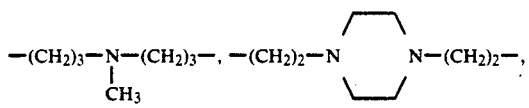

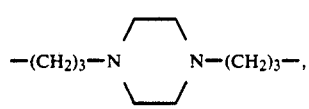

—(CH$_2$)$_3$O(CH$_2$)$_2$O(CH$_2$)$_3$—,

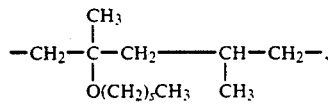

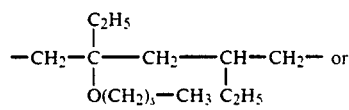

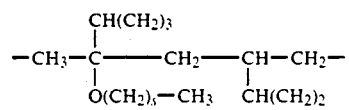

with s=0 to 7.

Preferred meanings for R$^3$ are hydrogen, straight-chain and branched C$_1$-C$_8$-alkyl, cyclohexyl, benzyl, phenyl and the radicals doubled via the bridge A, i.e, when R$^2$ is (a), a radical of the formula

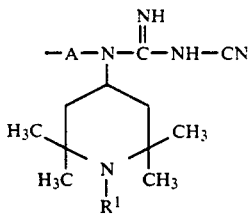

when R$^2$ is (b), a radical of the formula

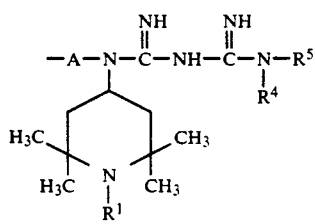

and when R$^2$ is (c), a radical of the formula

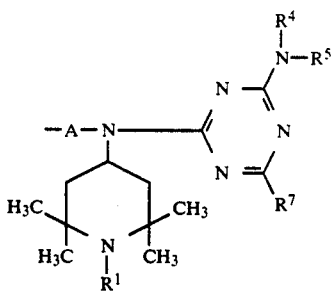

The bridge is preferably C$_2$-C$_8$-alkylene, especially 1,2-ethylene, 1,4-butylene, 1,6-hexylene or 1,8-octylene, also 1,4-cyclohexylidene or m- or p-phenylene.

Examples of meanings of R$^4$ and R$^5$ are, besides hydrogen, the following:

straight-chain and branched C$_1$-C$_{22}$-alkyl such as methyl, ethyl, n- and i-propyl, n- and i-butyl, n- and i-pentyl, hexyl, octyl, decyl, dodecyl, tetradecyl, hexadecyl, octadecyl, pivalyl, 3,3-dimethyl-2-butyl, neopentyl, 4-methyl-2-pentyl and 2-ethylhexyl;

C$_3$-C$_{22}$-alkenyl such as allyl, butenyl, pentenyl and oleyl;

C$_3$-C$_{12}$-cycloalkyl such as cyclopropyl, cyclobutyl, cyclopentyl, cyclohexyl, methylcyclohexyl, cycloheptyl, cyclooctyl, cyclododecyl and bicycloheptyl, of these cyclopentyl and, especially, cyclohexyl are preferred;

C$_3$-C$_{22}$-alkyl which is interrupted in the chain by oxygen or nitrogen atoms and which can additionally carry hydroxyl groups, such as —(CH$_2$)$_3$N(CH$_3$)$_2$, —(CH$_2$)$_3$N(C$_2$H$_5$)$_2$, —(CH$_2$)$_3$—OCH$_3$, —(CH$_2$)$_3$—O—CH(CH$_3$)$_2$, —(CH$_2$)$_2$—O—(CH$_2$)$_2$—OH, —CH$_2$—(CH$_2$)$_2$—CH$_2$—N(CH$_3$)$_2$, —(CH$_2$)$_2$—N[CH(CH$_3$)$_2$]$_2$, —(CH$_2$)$_2$—N(C$_2$H$_5$)$_2$, —(CH$_2$)$_2$—N(CH$_3$)$_2$, —(CH$_2$)$_2$—OCH$_3$ and —(CH$_2$)$_2$OCH$_2$CH$_3$;

substituted or unsubstituted C$_7$-C$_{22}$-phenyl- and diphenylalkyl such as benzyl, methoxybenzyl, methylbenzyl, ethylbenzyl, isopropylbenzyl, trimethylbenzyl, fluorobenzyl, chlorobenzyl, methylenedioxybenzyl, β-phenylethyl, γ-phenylpropyl and δ-phenylbutyl, dimethylaminobenzyl, diphenylmethyl and 1,3-diphenyl-2-propyl, where the substitution pattern on the phenyl can be o, m or p in each case;

phenyl and substituted phenyl such as 2-, 3- or 4-methylphenyl, 2-, 3- or 4-ethylphenyl, 2-, 3- or 4-n-propylphenyl, 2-, 3- or 4-iso-propylphenyl, 2-, 3- or 4-n-butylphenyl, 4-hexylphenyl, 4-octylphenyl, 4-dodecylphenyl, 2,3-dimethylphenyl, 2,6-dimethylphenyl, 2,4-dimethylphenyl, 2,4,6-trimethylphenyl, 2,3,5,6-tetramethylphenyl, 4-cyclohexylphenyl, 2-, 3- or 4-methoxyphenyl, 2-, 3- or 4-ethoxyphenyl, 2-, 3- or 4-propoxyphenyl, 2-, 3- or 4-butoxyphenyl, 4-hexoxyphenyl, 4-octoxyphenyl, 4-dodecoxyphenyl, 2-, 3- or 4-chlorophenyl, 2,3-dichlorophenyl, 2,4-dichlorophenyl, 2,6-dichlorophenyl, 4-hydroxyphenyl, 4-phenylphenyl, 4-benzylphenyl, 4-cyanophenyl, 4-methylaminophenyl, 4-dimethylaminophenyl, 4-ethylaminophenyl, 4-diethylaminophenyl,4-propylaminophenyl, 4-dipropylaminophenyl, 4-butylaminophenyl, 4-dibutylaminophenyl, 2-, 3- or 4-bromophenyl, 3,6-diethoxyphenyl, 3,6-dimethoxyphenyl, 2,4-dimethoxyphenyl, 3-chloro-6-methoxyphenyl, 2,4,5-trimethylphenyl, 2,5-dimethoxyphenyl, 2-methoxy-5-methylphenyl, 3,4-dimethoxyphenyl, 3,4-diethoxyphenyl, 3,5-dimethylphenyl;

5- or 6-membered heteroaromatic radicals such as 2-, 3- or 4-pyridyl, 2—(4,6-dimethyl)pyridyl, 2-(3-hydroxy)pyridyl, 1,3,4-thiadiazol-2-yl, 2-thiazolyl, 1,2,4-triazin-3-yl, 3-pyrazolyl, 2-pyrazinyl, or 3—(5-methyl)isoxazolyl, At least one of $R^4$ and $R^5$ is phenyl, substituted phenyl or a heteroaromatic radical.

In a preferred embodiment, one of $R^4$ and $R^5$ is hydrogen, straight-chain or branched $C_1$-$C_8$-alkyl, cyclohexyl or benzyl, and the other is phenyl, 4—$C_1$-$C_8$-alkylphenyl, 4-$C_1$-$C_8$-alkoxyphenyl, 4-chlorophenyl, 4-hydroxyphenyl or 4-cyanophenyl.

Examples of meanings of $R^6$ are, besides hydrogen, the following:

$C_1$-$C_{22}$-alkyl such as methyl, ethyl, n- and i-propyl, n- and i-butyl, n- and i-pentyl, hexyl, octyl, decyl, dodecyl, tetradecyl, hexadecyl, octadecyl, pivalyl, neopentyl or 2-ethylhexyl;

$C_2$-$C_{22}$-alkenyl such as vinyl, allyl, butenyl, pentenyl or oleyl;

$C_3$-$C_{12}$-cycloalkyl such as cyclopropyl, cyclopentyl, cyclohexyl, methylcyclohexyl or cycloheptyl, of which cyclopentyl and, especially, cyclohexyl are preferred;

$C_7$-$C_{22}$-phenyl- and diphenylalkyl such as benzyl, methyl benzyl, β-phenylethyl, γ-phenylpropyl, δ-phenylbutyl, carboethoxybenzyl, carbomethoxybenzyl or ethoxybenzyl, where the substitution pattern on the phenyl can be o, m or p in each case;

phenyl and substituted phenyl such as 2-, 3- or 4-methylphenyl, 2-, 3- or 4-ethylphenyl, 2-, 3- or 4-n-propylphenyl, 2-, 3- or 4-iso-propylphenyl, 2-, 3- or 4-n-butylphenyl, 4-hexylphenyl, 4-octylphenyl, 4-dodecylphenyl, 2,3-dimethylphenyl, 2,6-dimethylphenyl, 2,4-dimethylphenyl, 2,4,6-trimethylphenyl, 4-cyclohexylphenyl, 2-, 3- or 4-methoxyphenyl, 2-, 3- or 4-ethoxyphenyl, 2-, 3- or 4-propoxyphenyl, 2-, 3- or 4-butoxyphenyl, 4-hexoxyphenyl, 4-octoxyphenyl, 4-dodecoxyphenyl, 2-, 3- or 4-chlorophenyl, 2,3-dichlorophenyl, 2,4-dichlorophenyl, 2,6-dichlorophenyl, 4-hydroxyphenyl, 4-phenylphenyl, 4-benzylphenyl, 4-cyanophenyl, 4-methylaminophenyl, 4-dimethylaminophenyl, 4-ethylaminophenyl, 4-diethylaminophenyl, 4-propylaminophenyl, 4-dipropylaminophenyl, 4-butylaminophenyl, 4-dibutylaminophenyl, 2-, 3- or 4-bromophenyl, 3,6-diethoxyphenyl, 3,6-dimethoxyphenyl, 2,4-dimethoxyphenyl, 3-chloro-6-methoxyphenyl, 2,4,5-trimethylphenyl, 2,5-dimethoxyphenyl, 2-methoxy-5-methylphenyl, 3,4-dimethoxyphenyl, 3,4-diethoxyphenyl, 3,5-dimethylphenyl, 3- or 4-carbomethoxyphenyl, 3- or 4-carboethoxyphenyl, 3- or 4-carbopropoxyphenyl, 3-or 4-carbobutoxyphenyl, 3- or 4-carbohexoxyphenyl, 3- or 4-carboheptoxyphenyl, 3- or 4-carbooctoxyphenyl or 3- or 4-carbo-2-ethylhexoxyphenyl;

pyridyl;

$C_2$-$C_{22}$-alkyl interrupted by carbonyloxy, such as

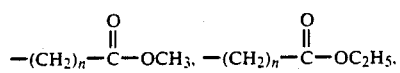

-continued

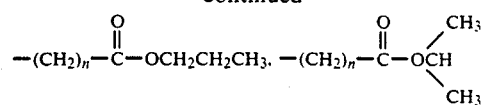

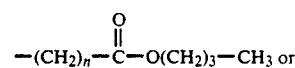

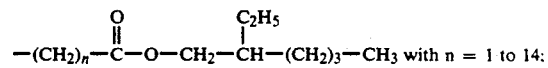

with n = 1 to 14;

a radical of the formula

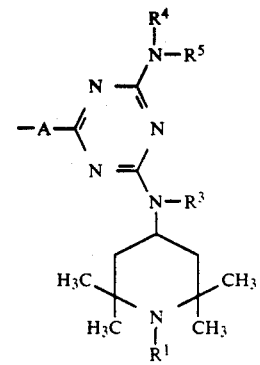

where the bridge A has the abovementioned meanings.

Preferred meanings of $R^6$ are hydrogen, straight-chain and branched $C_1$-$C_8$-alkyl, phenyl, benzyl, cyclohexyl and the radicals doubled via the bridge A, of the formula

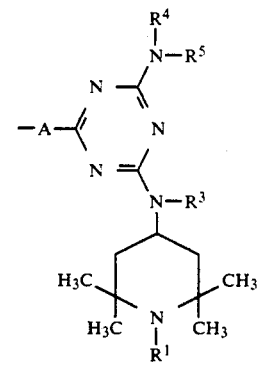

The novel polyalkylpiperidine derivatives where $R^2$ is a radical of the formula (a) can be prepared advantageously by conventional reactions of amines of the formula III or IIIa

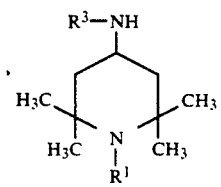

III

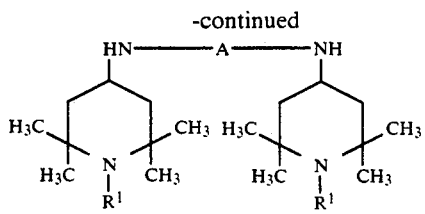   IIIa

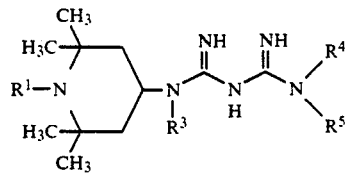   Ib with sodium dicyanamide. Reactions of this type are described, for example, in J. Chem. Soc. (1948) 1630–1636 (2). The amines III and IIIa are disclosed, for example, in EP-A 316 582 (3).

The reaction can be carried out in water and in organic solvents, preferably alcohols, especially n-butanol, or in mixtures thereof. The reaction is normally carried out in an acid medium, preferably in hydrochloric acid, at from about 60° to about 150° C.

Depending on the substituents and solvents, the compounds Ia can also be tautomerized to some extent, in accordance with the following equilibrium:

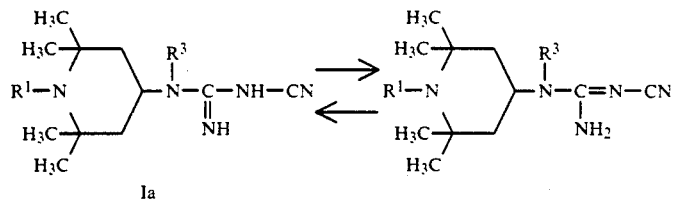

Analogous tautomeric forms are also possible for the polyalkylpiperidine derivatives where $R^2$ is a radical of the formula (b).

The novel biguanide derivatives of the formula Ib can be prepared advantageously by conventional reactions from the cyanoquanidines Ia

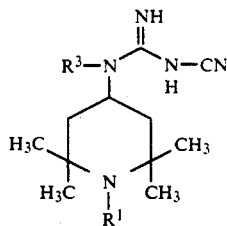   Ia and amines of the formula $HNR^4R^5$. Reactions of this type are described, for example, in the review article entitled The Chemistry of Biguanides in Fortschr. Chem. Forsch. 10 (1968) 375–472 (4).

The reaction can be carried out in water and in organic solvents, preferably alcohols, especially methanol, ethanol, n-propanol, iso-propanol, n-butanol and iso-butanol, or in mixtures thereof. It is normally carried out in an acid medium, preferably in hydrochloric acid, at from about 60° to about 150° C.

The novel polyalkylpiperidine derivatives where $R^2$ is a radical of the formula (c) can be prepared advantageously by the reactions disclosed in (4) of biguanides Ib and carboxylic acids or derivatives thereof of the formula $R^6$—COX, $R^6$—CN, XOC—A—COX, NC—A—COX or NC—A—CN where X is hydroxyl, chlorine, bromine or $C_1$–$C_4$-alkoxy.

Carboxylic acids or derivatives thereof which can be employed are, in particular, monobasic or dibasic carboxylic acids such as formic acid, acetic acid, succinic acid or adipic acid, the halides thereof, such as acetyl chloride, isobutyryl chloride, benzoyl chloride or benzoyl bromide, the esters thereof, such as methyl acetate, ethyl acetate, methyl propionate or methyl butyrate, methyl isobutyrate, methyl benzoate, dimethyl succinate, dimethyl adipate, dimethyl suberate or dimethyl sebacate, and the nitriles thereof such as acetonitrile or succinonitrile.

The reaction of the biguanides with the carboxylic acids or derivatives thereof can take place in water, in an organic solvent or in mixtures thereof. Possible organic solvents are alcohols such as methanol, ethanol, n-propanol, i-propanol, n-butanol, ethylene glycol or i-butanol. However, ethers are also suitable, e.g. glycol monobutyl ether, glycol dimethyl ether and glycol dibutyl ether. It is likewise possible to use aromatic hydrocarbons such as benzene, toluene, xylene or mesitylene. It is often advantageous to use one reactant as solvent if it is a liquid, for example the carboxylic esters such as ethyl acetate, methyl propionate or dimethyl adipate, or carboxylic acids such as formic acid.

The reaction is expediently carried out in the presence of a base such as sodium methylate, sodium ethylate, triethylamine, tributylamine, sodium hydroxide solution, potassium hydroxide solution, sodium carbonate or potassium carbonate. The reaction is normally carried out at from about 60° to about 150° C.

A multi-stage preparation of the triazines Ic is particularly advantageous

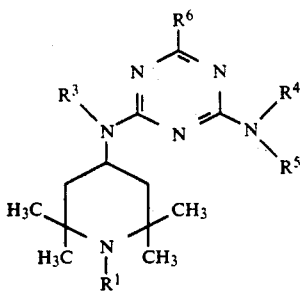

Ic and starts from the amines III or IIIa using the reaction steps described above.

The novel polyalkylpiperidine derivatives where $R^2$ is a radical of the formula (a) or (b) are valuable intermediates for preparing triazine derivatives Ic, which are mainly used as stabilizers and UV absorbers for organic material, and for other potential stabilizers and UV absorbers.

The novel compounds I can be in the form of the free bases or of acid addition salts. Suitable anions are derived, for example, from inorganic acids and, especially, from organic carboxylic and sulfonic acids.

Examples of inorganic anions are chloride, bromide, sulfate, dicyanamide, methosulfate, tetrafluoroborate, phosphate and thiocyanate.

Examples of suitable carboxylate anions are formate, acetate, propionate, hexanoate, cyclohexanecarboxylate, lactate, stearate, dodecylbenzoate, acrylate, methacrylate, citrate, malonate or succinate, and anions of polycarboxylic acids with up to 3000 COOH groups.

Examples of sulfonate anions are benzenesulfonate or tosylate.

The novel polyalkylpiperidine derivatives where $R^2$ is a radical of the formula (a) or (c) are exceptionally suitable for stabilizing organic material against the action of light, oxygen and heat. They are also effective inactivators of metals. They are added to the organic material which is to be stabilized in a concentration of from 0.01 to 5%, preferably from 0.02 to 1%, of the weight of the organic material, before, during or after its production.

Examples of organic materials are cosmetic products such as ointments and lotions, drug formulations such as pills and suppositories or precursors for plastics and coating compositions, but especially for plastic and coating compositions themselves.

The present invention also relates to organic material stabilized against the action of light, oxygen and heat, especially plastic and coating compositions, which contains the compounds Ia or Ic in the above-mentioned concentrations.

All conventional apparatus and methods for mixing stabilizers or other additives with polymers can be used for mixing the novel compounds Ia or Ic with, in particular, plastics.

Organic material stabilized with the novel compounds Ia and Ic can also contain further additives, e.g. antioxidants, light stabilizers, metal inactivators, antistatic agents, flameproofing agents, pigments and fillers.

Antioxidants and light stabilizers, which can be added besides the novel compounds, are, for example, compounds based on sterically hindered phenols or sulfur- or phosphorus-containing co-stabilizers.

Examples of phenolic antioxidants of this type are 2,6-di-tert-butyl-4-methylphenol, n-octadecyl $\beta$-(3,5-di-tert-butyl-4-hydroxyphenyl)propionate, 1,1,3-tris(2-methyl-4-hydroxy-5-tert-butylphenyl)butane, 1,3,5-trimethyl-2,4,6-tris(3,5-di-tert-butyl-4-hydroxybenzyl)-benzene, tris(3,5-di-tert-butyl-4-hydroxybenzyl) isocyanurate, tris[$\beta$-(3,5-di-tert-butyl-4-hydroxyphenyl)propionylethyl]isocyanurate, tris(2,6-dimethyl-3-hydroxy4-tert-butylbenzyl) isocyanurate and pentaerythritol tetrakis[$\beta$-(3,5-di-tert-butyl-4-hydroxyphenyl)-propionate].

Examples of suitable phosphorus-containing antioxidants are tris(nonylphenyl) phosphite, distearylpentaerythritol diphosphite, tris(2,4-di-tert-butylphenyl) phosphite, tris(2-tert-butyl-4-methylphenyl) phosphite, bis(2,4-di-tert-butylphenyl) pentaerythritol diphosphite and tetrakis(2,4-di-tert-butylphenyl) 4,4'-biphenylenediphosphite.

Examples of sulfur-containing antioxidants are dilauryl thiodipropionate, dimyristyl thiodipropionate, distearyl thiodipropionate, pentaerythritol tetrakis($\beta$-laurylthiopropionate) and pentaerythritol tetrakis($\beta$-hexylthiopropionate).

Examples of other antioxidants and light stabilizers which can be used together with the novel compounds are 2—(2-hydroxyphenyl)benzotriazoles, 2-hydroxybenzophenones, aryl hydroxybenzoates, $\alpha$-cyanocinnamic acid derivatives, benzimidazolecarboxanilides, nickel compounds or oxanilides.

Examples of plastics which can be stabilized by the novel compounds Ia and Ic are:

polymers of mono- and diolefins such as low or high density polyethylene, polypropylene, linear poly-1-butene, polyisoprene, polybutadiene and copolymers of mono- or diolefins or mixtures of the said polymers;

copolymers of mono- or diolefins with other vinyl monomers such as ethylene/alkyl acrylate copolymers, ethylene/alkyl methacrylate copolymers, ethylene/-vinyl acetate copolymers or ethylene/acrylic acid copolymers; polystyrenes;

copolymers of styrene or $\alpha$-methylstyrene with dienes and/or acrylic derivatives such as styrene/butadiene, styrene/acrylonitrile (SAN), styrene/ethyl methacrylate, styrene/butadiene/ethyl acrylate, styrene/acrylonitrile/methacrylate, acrylonitrile/butadiene/styrene (ABS) or methyl methacrylate/butadiene/styrene (MBS);

halogenated polymers such as polyvinyl chloride, polyvinyl fluoride, polyvinylidene fluoride and copolymers thereof;

polymers derived from $\alpha,\beta$-unsaturated acids and derivatives thereof such as polyacrylates, polymethacrylates, polyacrylamides and polyacrylonitriles;

polymers derived from unsaturated alcohols and amines or from acrylic derivatives or acetals thereof, e.g. polyvinyl alcohol and polyvinyl acetate;

polyurethanes, polyamides, polyureas, polyesters, polycarbonates, polysulfones, polyether-sulfones and polyether-ketones.

The novel compounds Ia and Ic can also be used to stabilize surface coatings, e.g. industrial coatings, particularly baking finishes and especially automotive coatings, preferably two-layer coatings.

The novel compounds Ia and Ic can be added to the coating composition in solid or dissolved form. It is particularly advantageous that they are readily soluble in coating systems.

The novel compounds Ia and Ic are preferably used for stabilizing polyamides and ABS and SAN polymers, especially molding compositions.

Another preferred area of use is the stabilization of polypropylene and polyamide, especially fibers thereof.

The novel compounds Ia and Ic are very compatible with conventional types of plastics and are readily soluble in conventional coating systems. Their intrinsic color is usually non-existent or negligible, they are stable and involatile at the temperatures conventionally used for processing plastics and surface coatings, and in particular they protect the materials treated with them for a long time.

PREPARATION EXAMPLES

Example 1a 53.4 g of 2,2,6,6-tetramethyl-4-aminopiperidine, 53.4 g of sodium dicyanamide and 54 g of concentrated hydrochloric acid were refluxed in 150 ml of water for 60 h. Filtration with suction, washing with water and methanol and drying under reduced pressure resulted in 80.1 g of the compound of the formula

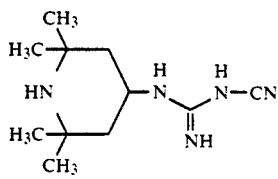

being obtained as a colorless solid of melting point 266°–267° C.

Calculated: C 59.2, H 9.5, N 31.4, Found: C 58.7, H 9.4, N 31.4.

Example Ib 42.1 g of 2,2,6,6-tetramethyl-4-aminopiperidine, 26.7 g of sodium dicyanamide and 27 g of concentrated hydrochloric acid were refluxed in 200 ml of n-butanol for 20 h. After cooling, the precipitate was filtered off with suction, washed with 200 ml of ethanol, boiled in 300 ml of water and dried. 45.6 g of the compound of Example Ia were obtained, melting point 266°–267° C.

Example 2

116.8 g of 4-n-butylamino-2,2,6,6-tetramethylpiperidine, 53.4 g of sodium dicyanamide and 55 g of concentrated hydrochloric acid were boiled in 150 ml of water for 8 h. After cooling and leaving to stand, a semicrystalline precipitate separated out. The water was decanted off and the residue was taken up in 150 ml of hot ethanol, the solution was filtered and cooled and then the precipitate was filtered off with suction. 69.1 g of the compound of the formula

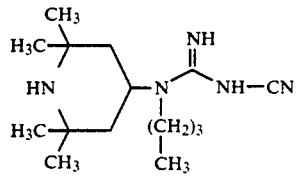

were obtained as a colorless solid of melting point 188°–189° C.

Calculated: C 64.5, H 10.5, N 25.1, Found: C 64.2, H 10.6, N 25.0.

Example 3

60.0 g of 4-n-hexylamino-2,2,6,6-tetramethylpiperidine, 39.7 g of sodium dicyanamide and 25 g of concentrated hydrochloric acid were refluxed in 150 ml of water for 15 h. After cooling and addition of 10 ml of 50% strength sodium hydroxide solution, the precipitate was filtered off with suction, washed with water and recrystallized from acetonitrile. 62 g of the compound of the formula

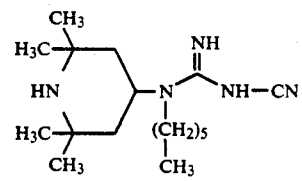

were obtained as a colorless solid of melting point 193°–194° C.

Calculated: C 66.4, H 10.8, N 22.8, Found: C 66.4, H 10.9, N 22.9.

Example 4

67.0 g of 4-n-octylamino-2,2,6,6-tetramethylpiperidine, 39.7 g of sodium dicyanamide and 25 g of concentrated hydrochloric acid were boiled in 150 ml of water for 13 h and worked up as in Example 3. 64 g of the compound of the formula

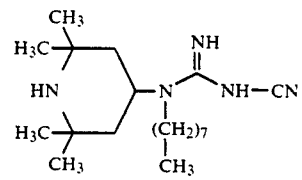

were obtained as a colorless solid of melting point 173°–175° C.

Calculated: C 68.0, H 11.1, N 20.9, Found: C 68.0, H 11.2, N 21.1.

Example 5

238 g of 4-cyclohexylamino-2,2,6,6-tetramethylne, 98 g of sodium dicyanamide and 100 g of concentrated hydrochloric acid were boiled for 10.5 h. After addition of 98 g of sodium dicyanamide and 50 ml of n-butanol, the reaction mixture was boiled for a further 14 h. After cooling, the precipitate was stirred in sodium hydroxide solution, filtered off with suction and recrystallized from acetonitrile. 140 g of the compound of the formula

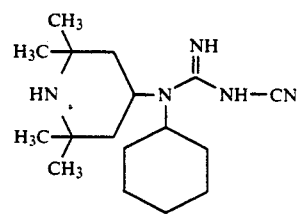

were obtained as a colorless solid of melting point 230°–233° C.

Calculated: C 66.8, H 10.2, N 22.9, Found: C 66.7, H 10.3, N 23.3.

Example 6

78.8 g of N,N'-bis(2,2,6,6-tetramethyl-4-piperidinyl)-1,6-hexamethylenediamine, 35.6 g of sodium dicyanamide and 40 g of concentrated hydrochloric acid were boiled in 130 ml of water for 4.5 h. After addition of 17 g of sodium dicyanamide and 20 g of concentrated hydrochloric acid, the reaction mixture was boiled for a further 8.5 h. After cooling, the precipitate was filtered off with suction and stirred in sodium hydroxide solution, then filtered off with suction, washed with water until neutral and recrystallized from dimethylformamide. 37 g of the compound of the formula

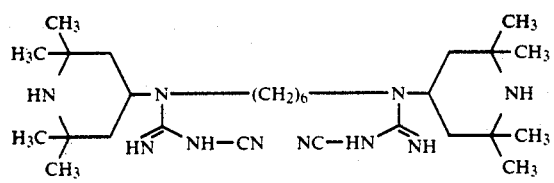

were obtained as a colorless solid of melting point 305°–306° C.

Calculated: C 63.6, H 9.9, N 26.5, Found: C 63.6, H 9.9, N 26.4.

Example 7

33.5 g of 2,2,6,6-tetramethyl-4-piperidinylcyanoguanidine from Example 1, 18.4 g of p-anisidine and 25 ml of concentrated hydrochloric acid were boiled in 100 ml of water for 5 h. The solution was filtered and the filtrate was made alkaline with sodium hydroxide solution. The precipitate was filtered off with suction, dried and recrystallized from cyclohexane. 30 g of the product of the formula

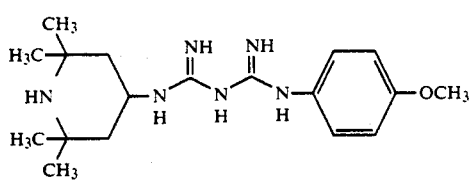

were obtained as a colorless solid of melting point 132°–136° C.

Example 8

44.6 g of 2,2,6,6-tetramethyl-4-piperidinylcyanoguanidine from Example 1, 26.5 g of p-chloroaniline and 40 g of concentrated hydrochloric acid were boiled in 100 ml of water for 5 h. After cooling, the solution was made alkaline with sodium hydroxide solution. The aqueous phase was decanted off the oily precipitate, and the residue was stirred in a mixture of 150 ml of acetonitrile and 450 ml of water. The microcrystalline precipitate was filtered off with suction, dried and boiled with methylcyclohexane. 50 g of the compound of the formula

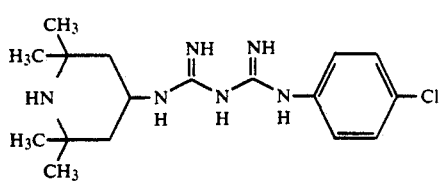

were obtained as a colorless solid of melting point 152°–155° C.

Example 9

44.6 g of 2,2,6,6-tetramethyl-4-piperidinylcyanoguanidine from Example 1, 18.6 g of aniline and 40 g of concentrated hydrochloric acid were boiled in 100 ml of water for 3 h. After addition of 100 g of ice, the mixture was made alkaline with sodium hydroxide solution, 150 ml of water were added and the mixture was stirred for 30 minutes. The precipitate was filtered off with suction, washed with water, dried and boiled with cyclohexane. 29 g of the compound of the formula

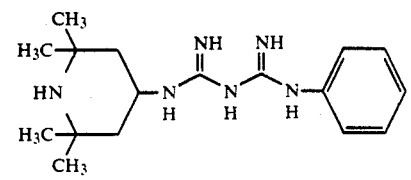

were obtained as a colorless solid of melting point 153°–156° C.

Example 10

44.6 g of 2,2,6,6-tetramethyl-4-piperidinylcyanoguanidine from Example 1, 21.4 g of p-toluidine and 40 g of concentrated hydrochloric acid were reacted and worked up as in Example 9. Recrystallization from toluene resulted in 29 g of the compound of the formula

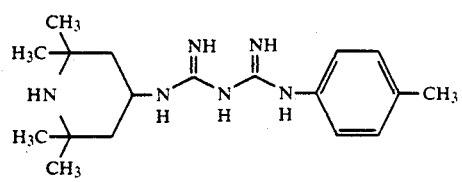

as a colorless solid of melting point 156°–158.C.

Example 11

100.3 g of 2,2,6,6-tetramethyl-4-piperidinylcyanoguanidine from Example 1, 61.6 g of p-phenetidine and 90 g of concentrated hydrochloric acid were reacted and worked up as in Example 9. Recrystallization from methylcyclohexane resulted in 52 g of the compound of the formula

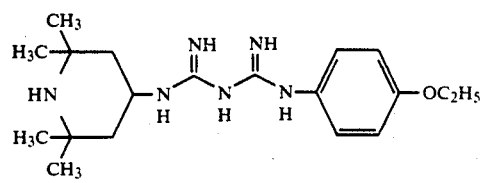

as a colorless solid of melting point 136°-131° C.

Example 12

50 g of N-octyl-N—(2,2,6,6-tetramethyl-4-piperidinyl)cyanoguanidine from Example 4, 20.4 g of p-phenetidine and 29.8 g of concentrated hydrochloric acid were boiled in 150 ml of water for 6 h. The solution was made alkaline with sodium hydroxide solution and extracted by shaking with dichloromethane. After phase separation, the organic solvent was removed under water pump vacuum, leaving a residue of the compound of the formula

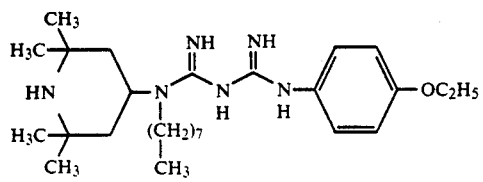

as a highly viscose oil.

Calculated: C 68.6, H 10.2, N 17.8, Found: C 68.5, H 10.5, N 17.8.

Example 13

48 g of N-hexyl-N—(2,2,6,6-tetramethyl-4-piperidinyl)cyanoguanidine from Example 3, 21.4 g of p-phenetidine and 31.2 g of concentrated hydrochloric acid were boiled in 150 ml of water for 5.5 h. While cooling, the mixture was made alkaline with sodium hydroxide solution, the aqueous phase was decanted off and the residue was dissolved in toluene. The toluene phase was washed with water and, after phase separation, the toluene was removed under water pump vacuum. The viscose residue weighed 50 g and had the following structure

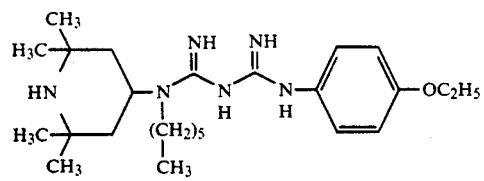

Example 14

24 g of N,N'-bis(cyanamidino)-N,N'-bis(2,2,6,6-tetramethyl-4-piperidinyl)-1,6-hexamethylenediamine from Example 6, 12.35 g of p-phenetidine and 18 g of concentrated hydrochloric acid were boiled in 125 ml of water for 8.5 h. While cooling in ice, the mixture was made alkaline with sodium hydroxide solution, and the precipitate was filtered off with suction, dried and recrystallized from methylcyclohexane with addition of active carbon. 22.6 g of the compound of the formula

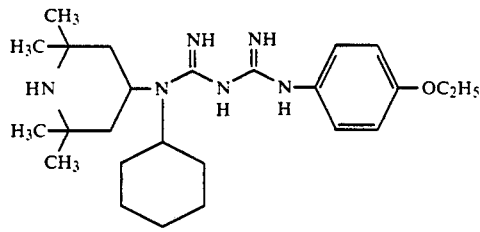

were obtained as a colorless solid of melting point 95°-97° C.

Example 15

50 g of N-cyclohexyl-N—(2,2,6,6-tetramethyl-4-piperidinyl)cyanoguanidine from Example 5, 22.5 g of p-phenetidine and 33 g of concentrated hydrochloric acid were boiled in 150 ml of water for 5.5 h. While cooling, the mixture was made alkaline with sodium hydroxide solution and extracted by shaking with dichloromethane. The organic phase was concentrated under water pump vacuum, and the residue was recrystallized from acetonitrile. 58 g of the compound of the formula

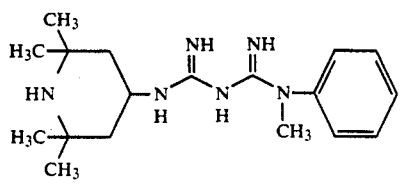

were obtained as a colorless solid of melting point 115°-116° C.

Example 16

66.9 g of 2,2,6,6-tetramethyl-4-piperidinylcyanoguanidine from Example 1, 32.1 g of N-methylaniline and 60 g of concentrated hydrochloric acid were boiled in 150 ml of water for 7.5 h. While cooling, the mixture was made strongly alkaline with sodium hydroxide solution, the aqueous phase was decanted off, and the residue was taken up in ethyl acetate. The organic phase was washed with water and then concentrated under water pump vacuum, and the residue was recrystallized from acetonitrile. 43 g of the compound of the formula were obtained as a colorless solid of melting point 135°-137° C.

Example 17

66.9 g of 2,2,6,6-tetramethyl-4-piperidinylcyanoguanidine from Example 1, 44.7 g of N-butylaniline and 60 g of concentrated hydrochloric acid were boiled in 150 ml of water for 7.5 h. The mixture was made strongly alkaline with sodium hydroxide solution. Addition of dichloromethane caused a precipitate to separate out, and this was filtered off. The methylene chloride phase was concentrated, when more precipitate separated out, and the two precipitates were combined and recrystallized from cyclohexane with the addition of active carbon. 62 g of the product of the formula

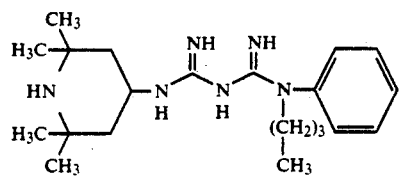

were obtained as a colorless solid of melting point 65°–68° C.

Example 18

35 g of 1—(2,2,6,6-tetramethyl-4-piperidinyl)-5-(p-chlorophenyl)biguanide from Example 8, 18 g of 30% by weight methanolic sodium methylate solution and 30.2 g of methyl isobutyrate were heated in 100 ml of toluene for 5 h, during which the low boilers were distilled out. After the boiling point had reached 110° C., 100 ml of water were added and the phases were separated hot. Cooling of the toluene phase resulted in a precipitate which was filtered off with suction and washed with a little acetonitrile. Drying resulted in 29.2 g of the compound of the formula

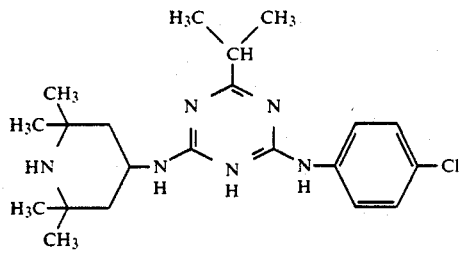

as a colorless solid of melting point 190-192° C.

Calculated: C 62.6, H 7.7, N 20.8, Cl 8.8, Found: C 62.9, H 7.8, N 20.7, Cl 8.6.

Example 19

100 ml of ethyl acetate were added, in such a way that the internal temperature was 105° C., to 26 g of 1-(2,2,6,6-tetramethyl-4-piperidinyl)-5—(p-methoxyphenyl)biguanide, prepared by reacting 2,2,6,6-tetramethyl-4-piperidinylcyanoguanidine from Example 1 with p-anisidine in a similar manner to Example 9, and 19 g of 30% by weight methanolic sodium methylate solution in 100 ml of toluene at an internal temperature of 110° C. while distilling out the low boilers over the course of 9 h. Working up was carried out as in Example 18, the toluene phase was treated with active carbon and magnesium sulfate, and then the toluene was distilled off under water pump vacuum. Recrystallization of the residue from acetonitrile resulted in 11.7 g of the compound of the formula

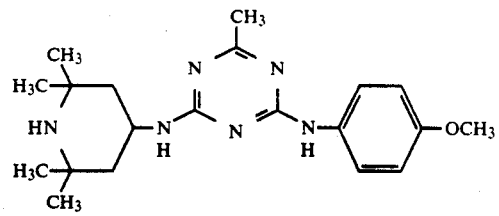

as a colorless solid of melting point 175°–177° C.

Calculated: C 64.8, H 8.2, N 22.7, Found: C 64.9, H 8.4, N 22.6.

Example 20

24.8 g of 1—(2,2,6,6-tetramethyl-4-piperidinyl)-5-(p-methylphenyl)biguanide from Example 10 and 13.5 g of a 30% by weight methanolic sodium methylate solution were refluxed in 75 ml of ethyl acetate for 4 h. After cooling, 150 ml of water were added, the phases were separated and the organic phase was dried over magnesium sulfate. After filtration and removal of the solvent by distillation under water pump vacuum, the residue was recrystallized from acetonitrile. 12.1 g of the compound of the formula

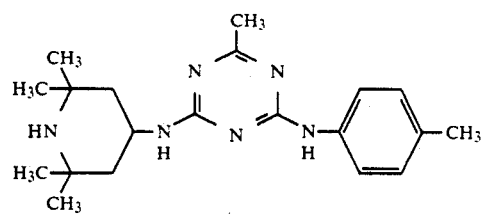

were obtained as a colorless solid of melting point 182°–184° C.

Calculated: C 67.8, H 8.5, N 23.7, Found: C 67.8, H 8.6, N 23.7.

Example 21

16.5 g of 1—(2,2,6,6-tetramethyl-4-piperidinyl)-5-(p-methylphenyl)biguanide from Example 10 and 9 g of a 30% by weight methanolic sodium methylate solution were heated at 125° C. in 190 ml of methyl benzoate for 4h. After cooling, 250 ml of petroleum ether were added, insolubles were filtered off, and the filtrate was concentrated. The residue was extracted twice by boiling with acetonitrile. 9.2 g of the compound of the formula

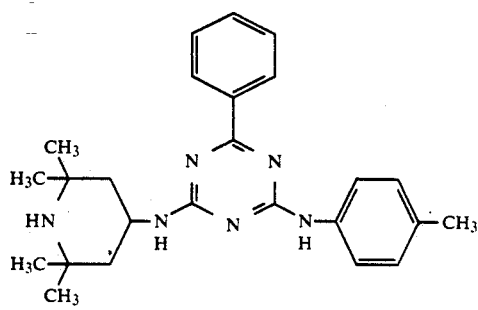

were obtained as a colorless solid of melting point 178°–180° C.

Calculated: C 72.1, H 7.7, N 20.2, Found: C 72.1, H 7.9, N 20.2.

Example 22

40 g of 1-butyl-1—(2,2,6,6-tetramethyl-4-piperidinyl)-5—(p-methylphenyl)biguanide, prepared by reacting N-hexyl-N—(2,2,6,6-tetramethyl-4-piperidinyl)-cyanoguanidine from Example 3 with p-toluidine in a similar manner to Example 9, 19 g of a 30% by weight methanolic sodium methylate solution and 10.8 g of methyl benzoate were heated in 150 ml of toluene for 9 h in a similar manner to Example 18. After cooling to room temperature, the mixture was filtered and the filtrate was concentrated under water pump vacuum. The residue was recrystallized twice from acetonitrile, resulting in 7.2 g of the compound of the formula

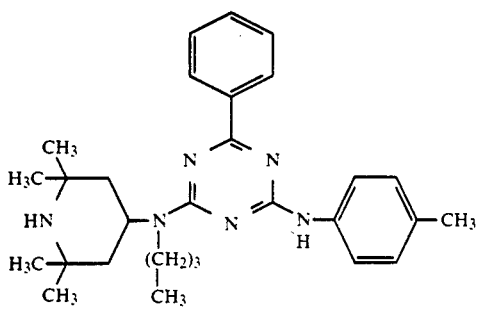

as a colorless solid of melting point 159°-161 C.

Calculated: C 73.7, H 8.5, N 17.8, Found: C 73.1, H 8.7, N 17.7.

Example 23

25 g of 1-hexyl-1—(2,2,6,6-tetramethyl-4-piperidinyl)-5—(p-ethoxyphenyl)biguanide from Example 13 were boiled in 50 ml of formic acid for 20 h. After cooling, the mixture was diluted with ice-water, made strongly alkaline with sodium hydroxide solution and extracted with dichloromethane. The organic phase was concentrated under water pump vacuum, and the residue was recrystallized from n-hexane. 17.5 g of the compound of the formula

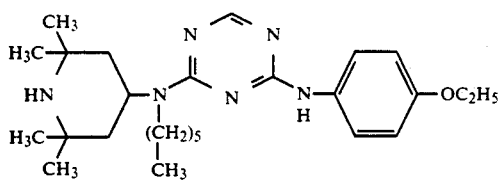

were obtained as a colorless solid of melting point 130°-132° C.

Calculated: C 68.7, H 9.3, N 18.5, Found: C 68.2, H 9.3, N 18.2.

Example 24

30 g of 1-octyl-1—(2,2,6,6-tetramethyl-4-piperidinyl)-5—(p-ethoxyphenyl)biguanide from Example 12 were reacted in 75 g of formic acid and worked up in a similar manner to Example 23. Recrystallization from acetonitrile resulted in 20.5 g of the compound of the formula

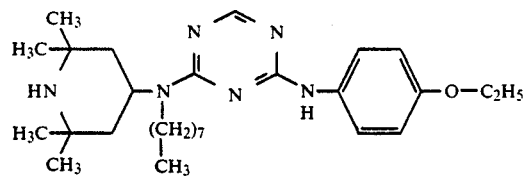

as a colorless solid of melting point 122°-130° C.

Calculated: C 69.7, H 9.6, N 17.4, Found: C 69.8, H 9.8, N 17.4.

Example 25

25 g of 1-hexyl-1—(2,2,6,6-tetramethyl-4-piperidinyl)-5—(p-ethoxyphenyl)biguanide from Example 13, 10.1 g of a 30% by weight methanolic sodium methylate solution and 3.8 g of dimethyl adipate were heated at 100° C. in 50 ml of ethylene glycol monobutyl ether for 35 h. After cooling, 25 ml of concentrated hydrochloric acid and, after standing overnight, 200 ml of water were added. After addition of sodium hydroxide solution, the alcoholic mixture was extracted with dichloromethane. The organic phase was concentrated under water pump vacuum and the residue was recrystallized from ethyl acetate. 4.6 g of the compound of the formula

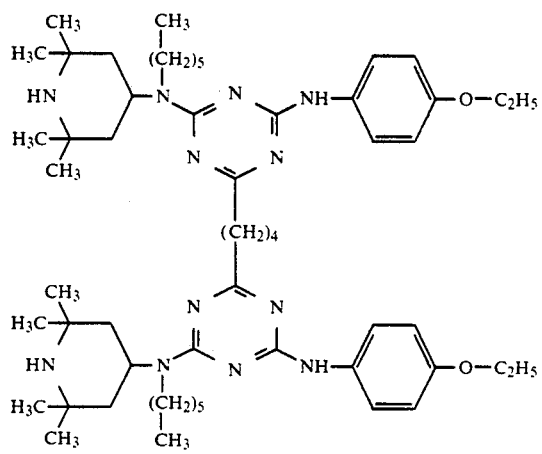

were obtained as a colorless solid of melting point 190°-191° C.

Calculated: C 69.8, H 9.4, N 17.4, Found: C 69.4 ,H 9.5, N 17.4.

We claim:

1. A compound of the formula I

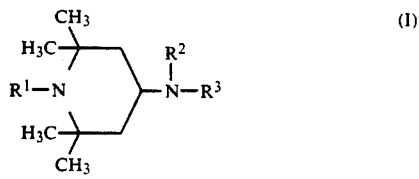

where

R$^1$ is a hydrogen, C$_1$-C$_8$-alkyl, phenyl- or tolylalkyl with 1 to 4 carbon atoms in the alkyl, C$_1$-C$_6$-acyl, benzoyl, allyl, cyanomethyl, hydroxyethyl, aminoethyl, hydroxyl or oxyl free radical, R$^2$ is a radical of the formula;

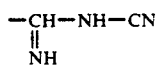

$R^3$ is hydrogen, $C_1$–$C_{22}$-alkyl, $C_3$–$C_{22}$-alkenyl, $C_7$–$C_{22}$-phenyl- and diphenylalkyl, where the phenyl can be unsubstituted or substituted one to three times by $C_1$–$C_{12}$-alkyl, $C_1$–$C_{12}$-alkoxy, fluorine, chlorine, bromine, $C_1$–$C_{12}$-alkylamino or $C_1$–$C_{22}$-dialkylamino, $C_3$–$C_{12}$-cycloalkyl or bicycloalkyl, $C_4$–$C_{22}$-alkyl which is interrupted by oxygen or nitrogen atoms ad which can additionally carry hydroxyl groups, phenyl which can be substituted by one to three methyl or carbo-$C_1$–$C_{12}$-alkoxy groups, or is $C_1$–$C_{22}$-alkyl containing heterocyclic radicals, selected from the group consisting of:

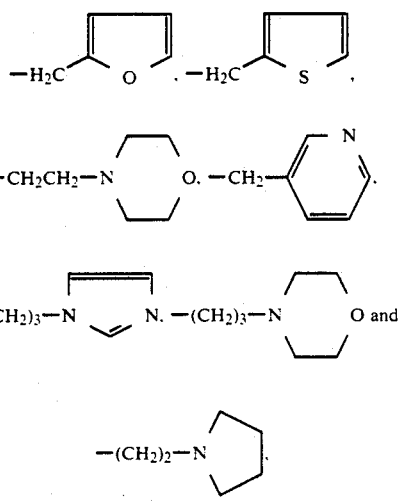

or is a radical of the formula:

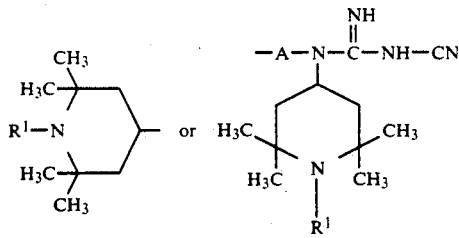

where A is $C_2$–$C_{22}$-alkylene, $C_5$–$C_{22}$-cycloalkylene, $C_8$–$C_{16}$-phenylalkylene, phenylene or $C_4$–$C_{30}$-alkylene which is interrupted in the chain by oxygen or nitrogen atoms or a radical of the formula:

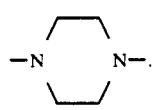

2. The compound of claim 1 which has the formula:

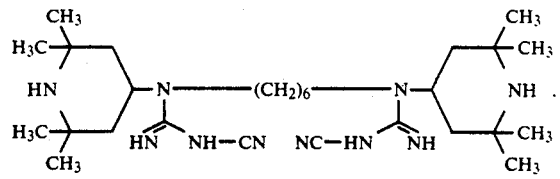

3. A compound according to claim 1, wherein the substituent $R^3$ is a $C_4$–$C_{22}$-alkyl which is interrupted by oxygen or nitrogen atoms and is selected from the group consisting of —$(CH_2)_3N(CH_3)_2$, —$CH_2)_3N(C_2H_5)_2$, —$(CH_2)_3$—$OCH_3$, —$(CH_2)_3$—$O$—$CH(CH_3)_2$, —$(CH_2)_2$—$O$—$H_2)_2$—$OH$, —$CH_2$—$(CH_2)_2$—$CH_2$—$N(CH_3)_2$, —$(CH_2)_2$—$N(CH(CH_3)_2)_2$, —$(CH_2)_2$—$N(C_2H_5)_2$, —$(CH_2)_2$—$N(CH_3)_2$, —$(CH_2)_2$—$OCH_3$ and —$(CH_2)_2OCH_2CH_3$.

4. A compound according to claim 1, wherein the substituent A is a $C_4$–$C_{30}$-alkylene which is interrupted in the chain by oxygen or nitrogen atoms or a piperazino radical and is selected from the group consisting of:

—$(CH_2)_3O(CH_2)_4O(CH_2)_3$—,
—$(CH_2)_3O(CH_2)_2O(CH_2)_2O(CH_2)_3$—,

—$(CH_2)_2\underset{\underset{CH_3}{|}}{N}$—$(CH_2)_2$—, —$(CH_3H_6O)_r$—$C_3H_6$— with r = 1 to 9, —$(CH_2)_3$—$\underset{\underset{CH_3}{|}}{N}$—$(CH_2)_3$—, —$(CH_2)_2$—N⟨ ⟩N—$(CH_2)_2$—,

—$(CH_2)_3$—N⟨ ⟩N—$(CH_2)_3$—,

—$(CH_2)_3O(CH_2)_2O(CH_2)_3$—, $$-CH_2-\underset{\underset{O(CH_2)_5CH_3}{|}}{\overset{\overset{CH_3}{|}}{C}}-CH_2-\underset{\underset{CH_3}{|}}{CH}-CH_2-,$$

$$-CH_2-\underset{\underset{O(CH_2)_5-CH_3}{|}}{\overset{\overset{C_2H_5}{|}}{C}}-CH_2-\underset{\underset{C_2H_5}{|}}{CH}-CH_2-\text{ or}$$

$$-CH_3-\underset{\underset{O(CH_2)_5-CH_3}{|}}{\overset{\overset{CH(CH_2)_3}{|}}{C}}-CH_2-\underset{\underset{CH(CH_2)_2}{|}}{CH}-CH_2-$$

with s=0 to 7.

5. A compound according to claim 1, wherein the substituent A is a $C_2$–$C_{22}$-alkylene or $C_5$–$C_{22}$-cycloalkylene radical selected from the group consisting of:

-continued
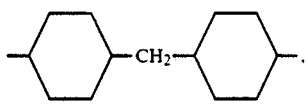
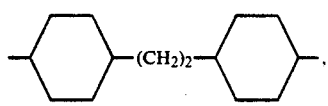
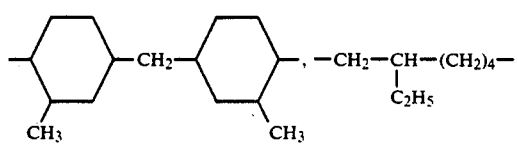
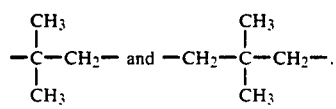
6. A compound according to claim 1, wherein the substituent A is a $C_8$–$C_{16}$-phenylalkylene or phenylene selected from the group consisting of:
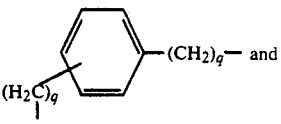
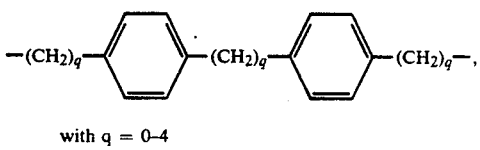
with q = 0–4
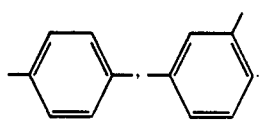
* * * * *